United States Patent [19]

Sarge, III et al.

[11] 4,120,747

[45] Oct. 17, 1978

[54] USE OF OZONE TREATED CHEMITHERMOMECHANICAL PULP IN A HIGH BULK TISSUE PAPERMAKING PROCESS

[75] Inventors: Henry David Sarge, III, Okeana; David Charles Kleinschmidt, Wyoming, both of Ohio

[73] Assignee: The Procter & Gamble Company, Cincinnati, Ohio

[21] Appl. No.: 817,073

[22] Filed: Jul. 18, 1977

Related U.S. Application Data

[63] Continuation-in-part of Ser. No. 554,378, Mar. 3, 1975, abandoned.

[51] Int. Cl.$^2$ .......................... D21B 1/12; D21C 9/00
[52] U.S. Cl. ..................................... 162/117; 162/142; 162/65; 162/25; 162/207
[58] Field of Search ................. 162/111, 112, 113, 23, 162/28, 206, 207, 65, 83, 84, 25, 117, 142

[56] References Cited

U.S. PATENT DOCUMENTS

| | | | |
|---|---|---|---|
| 3,301,746 | 1/1967 | Sanford et al. | 162/113 |
| 3,773,610 | 11/1973 | Shouvlin et al. | 162/25 |
| 3,821,068 | 6/1974 | Shaw | 162/111 |

FOREIGN PATENT DOCUMENTS 970,111  7/1975  Canada ..................................... 162/65

OTHER PUBLICATIONS

Soteland et al., *Norsk Skogindustri*, vol. 27 #10, 162/65, pp. 274–277.
Soteland et al., *Norsk Skogindustri*, 6/74, pp. 165–169.
Bohmer, E., "Norsk Skogindustri," pp. 249–252, 9/73.

*Primary Examiner*—S. Leon Bashore
*Assistant Examiner*—William F. Smith
*Attorney, Agent, or Firm*—Monte D. Witte; Fredrick H. Braun; John V. Gorman

[57] ABSTRACT

Soft, absorbent, bulky paper web useful in tissue, towel, sanitary, and like products. The web is formed by supplying an aqueous furnish which includes thermomechanically defibrated pulp in admixture with chemically defibrated pulp to a foraminous surface such as a Fourdrinier wire, transferring the moist web to an imprinting fabric, thermally drying the web without mechanical compression to a consistency of from about 30 percent to about 98 percent, imprinting the pattern of the fabric into the thermally predried web, and finally drying the web. The resulting web has relatively high tensile strength at relatively low density. Also, the strength properties of the web are significantly improved if the thermomechanically defibrated pulp is made from wood chips which have been soaked in chemical solutions prior to defibrating and then treated with ozone after defibrating.

8 Claims, 5 Drawing Figures

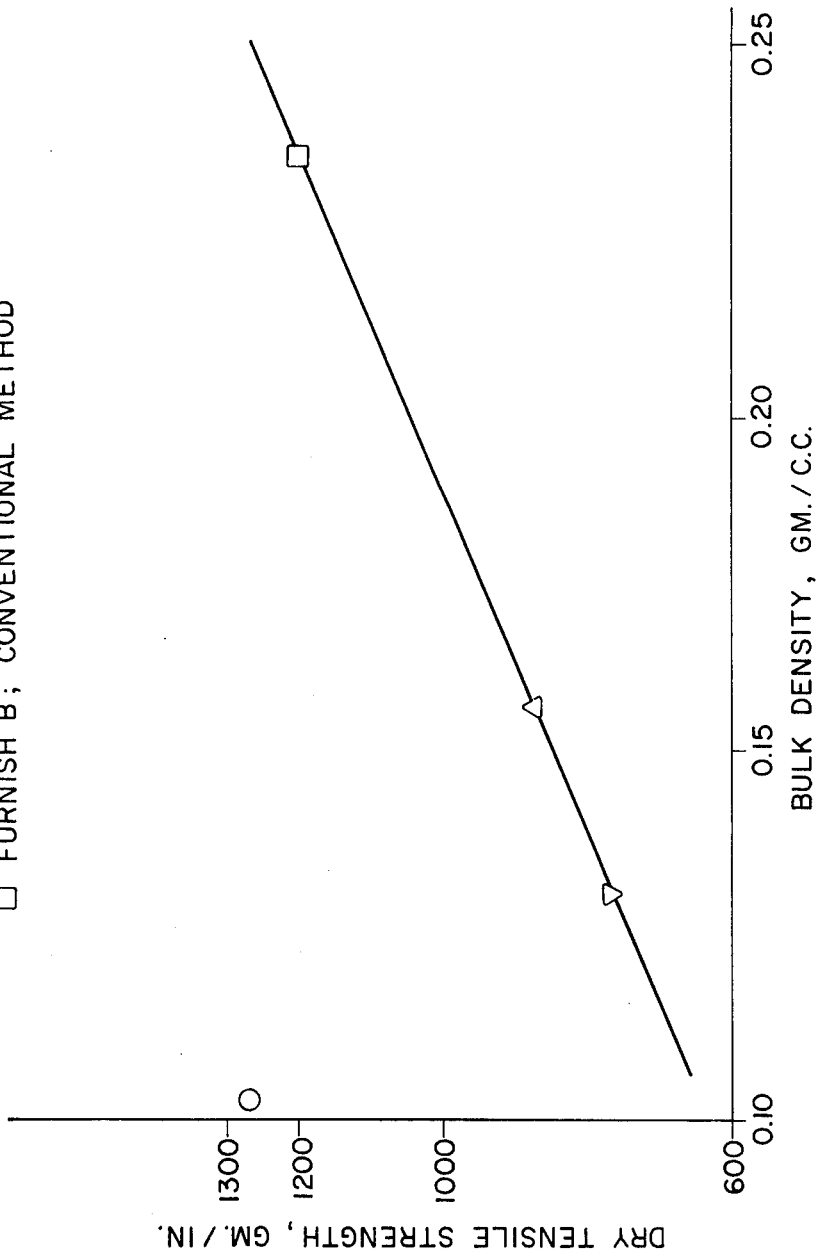

USE OF OZONE TREATED CHEMITHERMOMECHANICAL PULP IN A HIGH BULK TISSUE PAPERMAKING PROCESS

REFERENCE TO RELATED APPLICATION

This is a continuation-in-part of application Ser. No. 554,378 filed Mar. 3, 1975, abandoned.

BACKGROUND OF THE INVENTION

1. Field of the Invention

This invention relates to a soft and absorbent paper web useful in tissue, toweling, sanitary and like products and to methods for its manufacture.

2. Description of the Prior Art

Disposable paper articles such as tissues, towels, sanitary and like products made from bulky, absorbent paper webs are familiar articles of commerce. In the conventional manufacture of such products, it is customary to use paper webs which, during the manufacturing process, have been subjected to one or more pressing operations over the entire surface of the paper web, as laid down on the Fourdrinier wire or other forming surface, prior to final drying. In the conventional process, the pressing operations involve subjecting a moist paper web supported on a papermaking felt to pressure developed by opposing mechanical members such as rolls. While this operation expels water from the web thereby reducing the drying load, smoothing the surface of the web, and increasing its tensile strength, a paper of relatively high density and relatively stiff character is produced.

Various techniques have been suggested as improvements to the conventional papermaking process so that softer, bulkier and more absorbent paper webs can be made. One of the most significant such improvements is that described and claimed by Sanford and Sisson in U.S. Pat. No. 3,301,746 which issued Jan. 31, 1967. These inventors discovered that an improved, bulky, soft, absorbent paper web can be produced if the wet paper web is thermally predried without substantial compression to a fiber consistency substantially in excess of that normally found in webs entering the final thermal drying section of a conventional tissue papermaking process. The thermally predried web is imprinted with a knuckle pattern by a conveying and imprinting fabric, and finally dried without disturbing and imprinted knuckle pattern. The end result of this process, which is hereinafter referred to as the Sanford and Sisson process, is a sheet of tissue paper having lower apparent density and greater bulk than that which may be produced on a conventional paper machine while, at the same time, exhibiting adequate tensile strength for commercial uses of such paper.

Products made by either the conventional or the Sanford and Sisson process have been made using a variety of conventional wood pulps. The most common wood pulp used is that generally referred to as chemical pulp and is well known to those skilled in the papermaking art. This pulp consists essentially of delignified, relatively long, flexible fibers. Specific examples of these pulps are the well known kraft and sulfite pulps. While articles such as tissues, towels, and sanitary products made from conventional chemical pulps have found wide application among the consuming public, and while those made by the Sanford and Sisson process have received very favorable reception, two disadvantages are inherent in the use of conventional chemical pulps. First, there is the inability of manufacturers to further increase the absorbency, bulk, and softness of their products because of the inherent limitation of significantly decreased paper web tensile strength at desirable low densities. And second, there is the disadvantage associated with the inherent waste in chemical pulping operations. Conventional chemical pulping processes such as the well known kraft and sulfite processes yield only about 50 percent of the input wood as pulp and, concurrently, result in waste streams that either pollute the environment or are difficult and expensive to process so as to avoid pollution.

Two approaches have been used in an attempt to rectify the second disadvantage mentioned supra. The first of these is the use of conventional mechanical pulp in papermaking operations. (Conventional mechanical pulp is sometimes referred to as groundwood or stone ground pulp.) In this particular pulping operation, sections of the whole tree are comminuted in specially designed grinding machines. This process results in more than 90 percent of the input wood being emitted as pulp suitable for papermaking. This high yield, and absence of chemicals, substantially reduces the inherent waste and pollution problems associated with chemical pulping operations. Unfortunately, the conventional mechanical pulping operation results in pulp which is composed of relatively short fibers, highly damaged fibers, and large quantities of fiber and ligneous debris. Papers made from this pulp by any papermaking process are generally quite dense and stiff and are therefore unsuitable for use in consumer articles such as tissues, towels, sanitary and like products.

The second approach is a relatively recent improvement in mechanical pulping known as thermomechanical pulping. (This process is sometimes referred to as the pressure refining of wood fibers and as the Asplund process.) In this process, soaked wood chips are subjected to mechanical abrasion at temperatures in excess of the boiling point of water. It is postulated that the lignin binding the wood fibers is softened or plasticized by the elevated temperatures and the dissociation of the fibers is thereby facilitated. Pulps prepared by a normal thermomechanical pulping process are characterized by the relative freedom from damage of the individual fibers, the greater or lesser coating of the individual fibers with lignin, and the generally unmodified length of the fibers. As in conventional mechanical pulping processes, more than 90 percent of the wood entering the process is emitted as pulp suitable for papermaking and the potential for pollution caused by the process is greatly reduced as compared to normal chemical pulping methods.

Whereas conventional mechanically refined pulp has been found to be undesirable for use in absorbent, soft, bulky consumer articles such as tissues, towels, sanitary and like products, thermomechanically refined pulp can be used in conventional papermaking processes to produce such products. When thermomechanical pulp is used in conventional tissue papermaking processes to make low density paper webs, the relationship between web dry tensile strength and web density is the same as that relationship for conventional chemical pulps. That is to say, with conventional chemical pulps the decrease in tensile strength which occurs with decrease in web bulk density follows essentially a straight line relationship; substitution of thermomechanical pulp into the paper web, either as a portion of the fiber furnish or as the total fiber furnish, can be described by the same tensile-density relationship. The net result of the substitution of thermomechanical pulp into tissue, towel, sanitary and like products made by conventional papermaking processes and like products made by conventional papermaking processes is a improvement in the overall economy of such products and a reduction in the total pollution potential associated with manufacturing such products, but there is little resulting practical improvement in such products. (That is to say, there is little practical increase in bulk, softness, or absorbency because any decrease in density is accompanied by a corresponding decrease in tensile strength which makes the resulting products impractical to use.) The consumer products obtained using thermomechanical pulp in conventional papermaking processes are essentially identical to those which can be made with conventional chemical pulp.

SUMMARY OF THE INVENTION

It has now been surprisingly discovered that when thermomechanical pulp is used as a portion of the fiber furnish in the Sanford and Sisson process, paper webs are obtained which exhibit a tensile-density relationship which is significantly different from that which has been heretofore obtained using either conventional chemical pulp or thermomechanical pulp in conventional papermaking processes or only conventional chemical pulp in the Sanford and Sisson process. Enhanced web strength properties also result when ozone-treated chemi-thermomechanical pulp (hereinafter defined) is used as a portion of the furnish in the Sanford and Sisson process.

Accordingly, it is an object of this invention to provide paper webs for use in tissue, towel, sanitary and like products, said paper webs having significantly lower density (and, corresponding significantly higher bulk, greater absorbency, and enhanced softness) with relatively greater inherent dry tensile strength than has been heretofore possible.

It is a further object of this invention to provide a combination of process and starting material to successfully manufacture these improved paper webs.

Other objects and advantages of the invention will be evident from the following detailed description.

BRIEF DESCRIPTION OF THE DRAWINGS

FIG. 1B follows FIG. 1A in the processing sequence.

FIG. 2B follows FIG. 2A in the processing sequence.

FIG. 3 describes the tensile-density relationship of handsheets made from two fiber furnishes by conventional papermaking process and by the Sanford and Sisson process.

DETAILED DESCRIPTION OF THE INVENTION

Figure 1A:
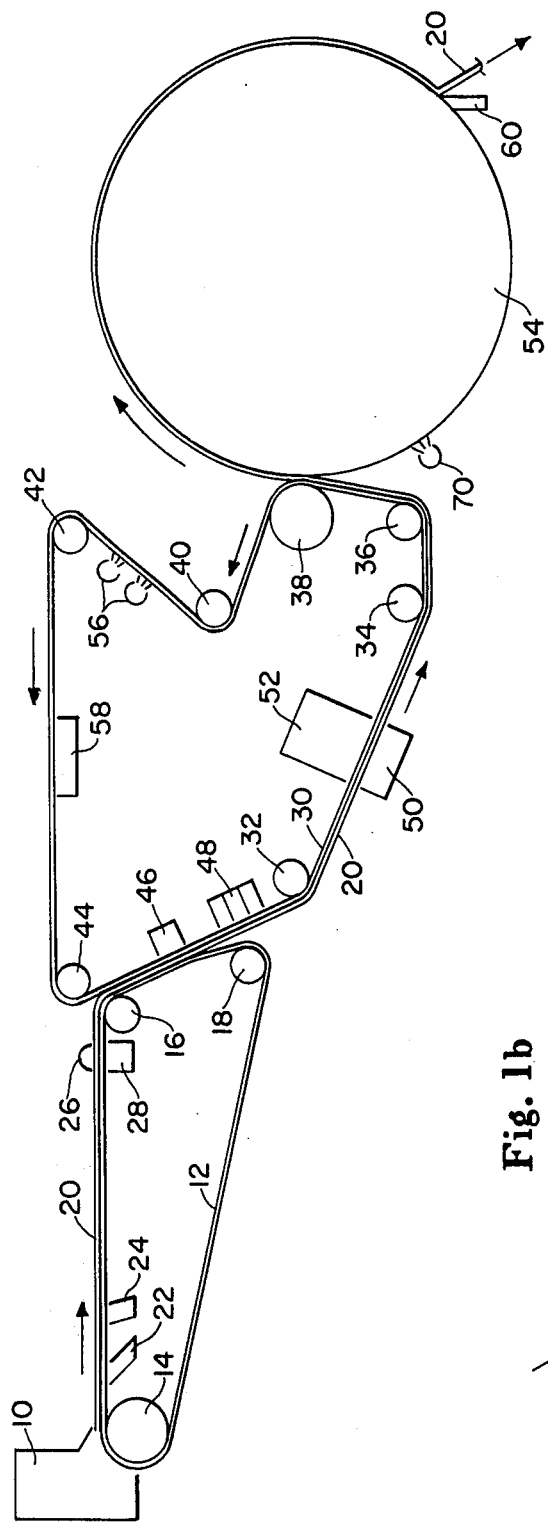
FIGS. 1A and 1B schematically illustrate an embodiment of the Sanford and Sisson process which can be used in the practice of the instant invention.

The net result of the practice of this invention is an absorbent paper web useful in tissue, towel, sanitary and like products. This absorbent paper web is made from a fiber furnish containing from about 5 to about 70 percent (based on dry weight of the total pulp) thermomechanical pulp as hereinafter defined in the furnish. The density of the web is from about 0.04 to about 0.15 g/cc, preferably from about 0.08 to about 0.10 g/cc. As used in this application, "density" is the bulk density of the web which is obtained by dividing the basis weight of the web by the caliper (apparent thickness) of the web. To obtain the bulk density in grams per cubic centimeter (g/cc), the basis weight of the web in pounds per 3,000 square feet is divided by the caliper in mils (thousandths of an inch) and that quotient is multiplied by the conversion factor 0.064. Caliper, or apparent web thickness, is measured with a motor-operated micrometer such as the Model 449-27, Series 400 micrometer manufactured by Testing Machines, Inc., of Amityville, New York. The caliper is measured under a load of 80 grams per square inch (12.40 grams per square centimeter) with an anvil 2 inches (5.08 cm) in diameter. Prior to measuring caliper, the web is conditioned at 73 ± 2° F. (22.8 ± 3.6° C.) at 50 ± 2 percent relative humidity.

Furthermore, the total dry tensile strength of the web is at least about 200 grams per inch of web width at a standard basis weight of 15.0 pounds per 3,000 square feet. As used herein, dry tensile strength is a measure of the ability of the web to resist tensile forces and is measured on a 1 inch (2.54 cm) wide strip of web, 4 inches (10.2 cm) long, which has been conditioned at a relative humidity of 50 ± 2 percent and a temperature of 73° ± 2° F. (22.8° ± 3.6° C.) Total tensile strength is the sum of the dry tensile strength of the web as measured in the machine direction and dry tensile strength of the web as measured in the cross-machine direction.

The absorbent paper web of this invention is obtained by use of the papermaking process described in U.S. Pat. No. 3,301,746 issued to Sanford and Sisson on Jan. 31, 1967, which patent is incorporated herein by reference. (As in the description of the prior art, supra, this process will be referred to as the Sanford and Sisson process.) The Sanford and Sisson process can be generally described as a series of steps comprising (1) forming an uncompacted paper web on a foraminous forming carrier, which can be a wire, a selected conveying and imprinting fabric, or a perforated belt; (2) supporting the uncompacted web on a conveying and imprinting fabric; (3) thermally predrying the uncompacted paper web to a selected fiber consistency; (4) imprinting the knuckle pattern of warp and weft cross-over points of a selected imprinting fabric into the thermally predried paper web; and (5) finally drying the imprinted paper web.

Figure 1B:
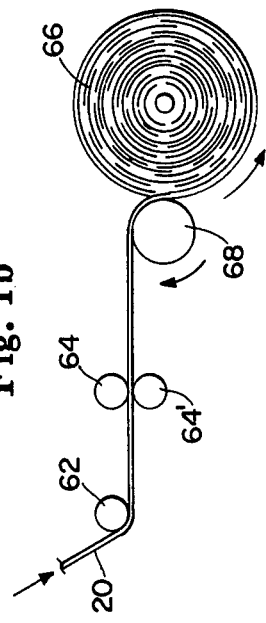

The following description, which makes continuing reference to FIGS. 1A and 1B, is of a preferred embodiment of the Sanford and Sisson process. The thickness of certain elements has been exaggerated for clarity. The precise details of the devices and apparatus used in the process will be readily apparent to those skilled in the art. It will also be apparent to those skilled in the art that numerous minor variations can be made in the described embodiment without departing from the spirit and scope of the Sanford and Sisson process.

Papermaking furnish comprising mixtures of fibers as hereinafter described is delivered from a closed headbox 10 to a Fourdrinier wire 12.

Fourdrinier wire 12 is supported by breast roll 14 adjacent to headbox 10 and couch roll 16 which is spaced from and horizontally aligned with breast roll 14. Return roll 18 is spaced downwardly and vertically offset from couch roll 16. The Fourdrinier wire 12 moves in the direction indicated by the arrow following a travel path established by rolls 14, 16 and 18. It passes over roll 14, moves horizontally toward roll 16, passes over roll 16 and moves downward toward roll 18, turns around and under roll 18, and then moves toward roll 14 and passes around and over roll 14.

Paper web 20 is formed on Fourdrinier wire 12 when furnish flows from headbox 10 onto Fourdrinier wire 12. The paper web formed has a dry basis weight ranging, for example, from about 5 to about 20 pounds per 3,000 square feet. The fiber consistency in the headbox ranges from about 0.1 percent to about 0.3 percent (by weight, dry fiber basis). After formation, the web travels with Fourdrinier wire 12 from breast roll 14 to and around couch roll 16 and continues with Fourdrinier wire 12 during a portion of the latter's path between couch roll 16 and return roll 18.

Forming devices 22 and 24 are positioned near breast roll 14 and respectively and successively bear on the underside of Fourdrinier wire 12 removing water from the web 20. Trimming nozzles 26 may be situated downstream of forming device 24 to trim the sides of the web. Vacuum box 28 is positioned under Fourdrinier wire 12 adjacent couch roll 16 so as to draw water from web 20 through Fourdrinier wire 12. As a result of the action of forming devices 22 and 24 and vacuum box 28, the web is dewatered to provide a fiber consistency ranging, for example, from about 10 to about 25 percent.

As Fourdrinier wire 12 is in that portion of its travel path between couch roll 16 and return roll 18, the partially dewatered web 20 is transferred to the conveying and imprinting fabric 30.

Conveying and imprinting fabric 30 moves in the direction indicated by the arrows along a path defined by a guide roll 32, a guide roll 34, a guide roll 36, a pressure roll 38, a guide roll 40, a guide roll 42 and a guide roll 44. In following its travel path, fabric 30 passes under guide roll 32, moves diagonally downward away from Fourdrinier wire 12, passes under guide roll 34, moves substantially horizontally toward guide roll 36, passes under guide roll 36 and turns upwardly thereabout, moves upward and passes over and around pressure roll 38, moves in the direction of Fourdrinier wire 12, passes under and around guide roll 40, moves diagonally upward in a direction away from Fourdrinier wire 12, passes over and around guide roll 42, moves substantially horizontally in a direction toward Fourdrinier wire 12, passes over and around guide roll 44 at a location adjacent couch roll 16, passes diagonally downward so as to be aligned with and adjacent the initial portion of the travel path of Fourdrinier wire 12 between couch roll 16 and return roll 18, and then passes under guide roll 32.

Conveying and imprinting fabric 30 is of a mesh structure and is formed of filament so that when a vacuum is exerted to force the moist web 20 against the fabric 30, the web 20 partially assumes the contour of the supporting surface of the fabric 30 including its knuckle pattern. This knuckle pattern is defined by the warp and weft cross-over points of imprinting fabric 30. The fabric can be a woven polyester monofilament such as described in U.S. Pat. No. 3,473,576 issued to Amneus on Oct. 21, 1969 or it can have the characteristics of the semi-twill fabric described in the U.S. Pat. No. 3,905,863 issued to Ayers on Sept. 16, 1975, both of said patents are commonly owned by the assignee of the present invention, and both of which are incorporated herein by reference. Preferably, the fabric 30 has its knuckle surfaces sanded in accordance with the teachings of U.S. Pat. No. 3,573,164 issued to Friedberg et al. on Mar. 30, 1971, which patent is commonly owned by the assignee of the present invention and which patent is incorporated herein by reference.

Moist web 20 is transferred from Fourdrinier wire 12 to imprinting fabric 30 by use of transfer vacuum box 46 positioned on the side of fabric 30 opposite Fourdrinier wire 12 between guide rolls 44 and 32. During the transfer operation, partially dewatered web 20 is separated from Fourdrinier wire 12 and is attached to fabric 30 and thereafter travels with fabric 30 through a portion of its travel path as hereinafter described.

Multi-stage vacuum box 48, depicted here as a three stage vacuum box containing compartments within which the vacuum is independently adjustable, is positioned on the side of fabric 30 opposite that in contact with web 20 and is located between transfer vacuum box 46 and guide roll 32. Multi-stage vacuum box 48 functions to partially dewater web 20.

As web 20 travels with fabric 30 between guide rolls 32 and 34, it is thermally dried. This drying must be accomplished without mechanically compacting the web 20. It is accomplished by using a hot air dryer 50 positioned on the same side of fabric 30 as is web 20 so that hot air may be directed against web 20 without tending to cause the intimate contact between web 20 and fabric 30 to be lessened. Preferably, hot air dryer 50 is of the type illustrated and described in U.S. Pat. No. 3,303,576 issued to Sisson on Feb. 14, 1967, which patent is commonly owned by the assignee of the present invention and which patent is herein incorporated by reference. An exhaust fan 52 is positioned adjacent dryer 50 so that web 20 and fabric 30 are interposed between dryer 50 and exhaust fan 52. This exhaust fan 52 serves to remove moisture as it evaporates from web 20. Thermal drying is performed on web 20 to increase the fiber consistency in web 20 above about 30 percent and preferably above about 60 percent and ranging up to as much as about 98 percent. That is to say, web 20 is dried to relatively high fiber consistencies without being subjected to mechanical compaction. Drying to relatively high fiber consistencies prior to imprinting against a rotating cylindrical surface, as hereinafter described, results in a reduced drying load on the hereinafter described Yankee dryer 54, a reduction which (1) reduces the residence time requirement of the web on Yankee dryer 54 thereby allowing an increase in line speed, or (2) allows a reduction in the required diameter of Yankee dryer 54 thereby leading to a direct and significant reduction in capital equipment cost.

Web 20, after having been thermally predried by dryer 50, continues with fabric 30 along its path under guide roll 34, under and around guide roll 36 and upwardly until both reach pressure roll 38 whereupon thermally dried web 20 is transferred to the rotating cylindrical surface of Yankee dryer 54.

As thermally predried web 20 is transferred to the rotating surface of Yankee dryer 54, which surface is rotated in the direction indicated by the arrow, it is imprinted with the knuckle pattern of imprinting fabric 30. This imprinting is accomplished by pressure roll 38 acting against fabric 30 and pressing web 20 against the rotating cylindrical surface of Yankee dryer 54.

After imprinting fabric 30 has been freed of thermally predried web 20, it is washed with water sprays 56, dried by vacuum box 58, and then follows its travel path over and around guide roll 44 to pick up uncompacted moist web 20 from Fourdrinier wire 12 to be imprinted in the manner previously described.

After web 20 has been transferred to the rotating cylindrical surface of Yankee dryer 54, it is dried to its final fiber consistency should it not already be at such consistency. It is then creped from the surface of Yankee dryer 54 by doctor blade 60. Web 20, while on rotating cylindrical surface of Yankee dryer 54, is generally exposed to a temperature in excess of 100° C. and normally less than about 180° C. After being removed from the rotating cylindrical surface of Yankee dryer 54 by doctor blade 60, the creped, dried web passes under guide roll 62, over a Mount Hope roll (not depicted), between calender rolls 64 and 64' which together make up a calender stack, and is wound on pick-up reel 66 which is driven by driving roll 68.

The transfer of thermally predried web 20 from imprinting fabric 30 to rotating cylindrical surface of Yankee dryer 54 is facilitated with the aid of a solution of adhering agent which is sprayed on the rotating cylindrical surface of Yankee dryer 54 prior to the point where thermally predried web 20 is transferred to said rotating cylindrical surface. The adhering agent solution, which improves the bond between the imprints of web 20 and the rotating cylindrical surface of Yankee dryer 54, is applied to the rotating cylindrical surface by adhering agent solution applicator 70. Applicator 70, which is not described in detail, can be any applicator means well known to those skilled in the art such as, for example, a spray nozzle supplied with adhering solution by means of a positive displacement pump. Adhering agents suitable for use in the instant invention include those comprising animal glue and well known to those skilled in the art. Additionally, novel and preferred adhering agents are described in U.S. Pat. No. 3,926,716, issued to Bates Dec. 16, 1975, which patent is owned by the assignee of the present invention and which patent is incorporated herein by reference. This preferred adhering agent is an aqueous solution of polyvinyl alcohol characterized by a degree of hydrolysis ranging from about 80 percent to about 90 percent and a viscosity, as a 4 percent aqueous solution at 20° C., exceeding about 20 centipoise. Most preferably, the polyvinyl alcohol is characterized by a degree of hydrolysis ranging from about 86 percent to about 90 percent and a viscosity, as a 4 percent aqueous solution at 20° C., above 35 centipoise.

The foregoing description of an embodiment of the Sanford and Sisson process is of necessity brief. Complete descriptions of the process and its permissible variations are contained in the above incorporated patents. In addition, certain modifications and adjustments of the process will be apparent to those skilled in the art.

Figure 2A:
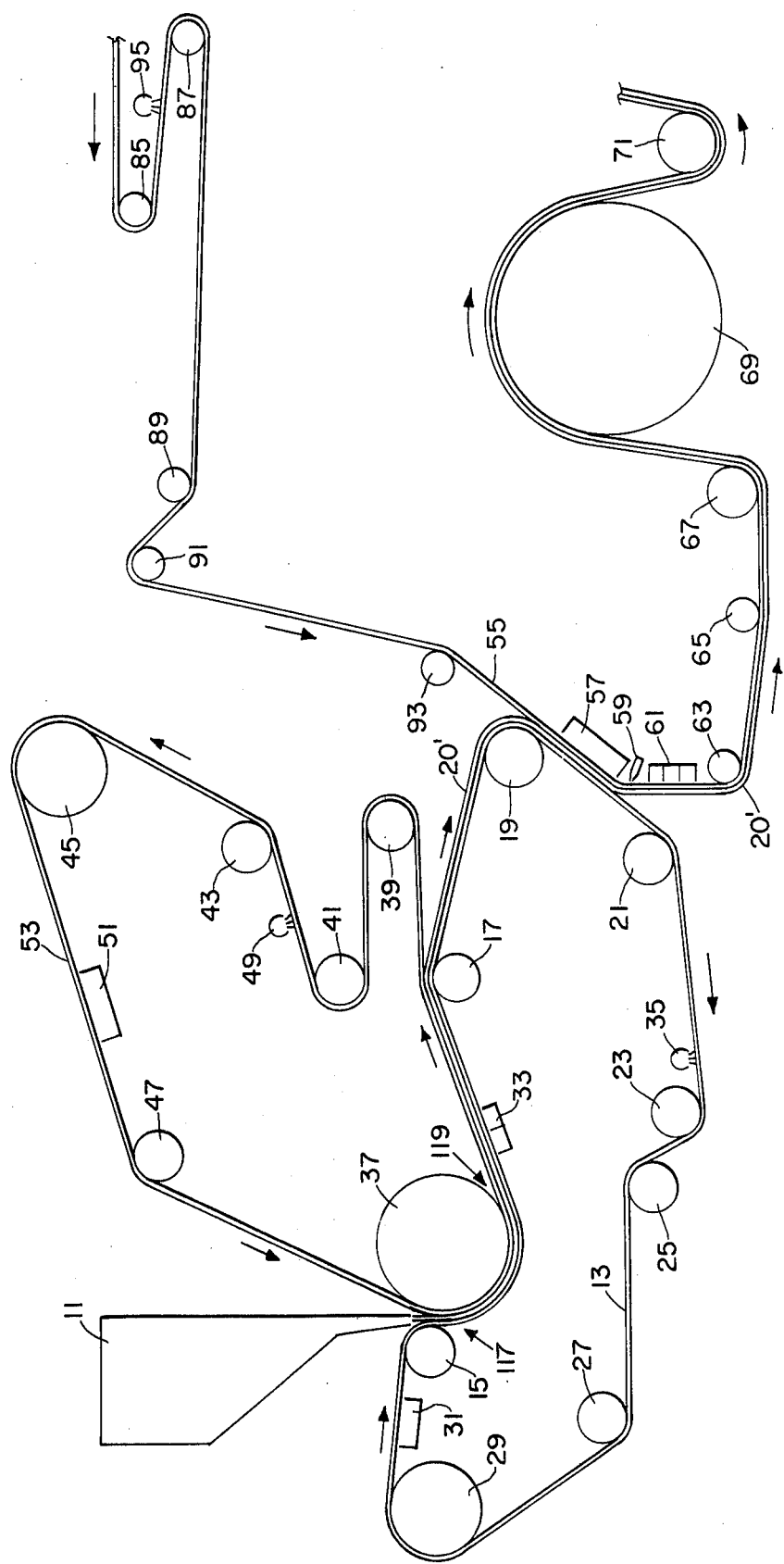
FIGS. 2A and 2B schematically illustrate another embodiment of the Sanford and Sisson process as practiced in conjunction with a well known twin-wire paper forming machine.
Figure 2B:
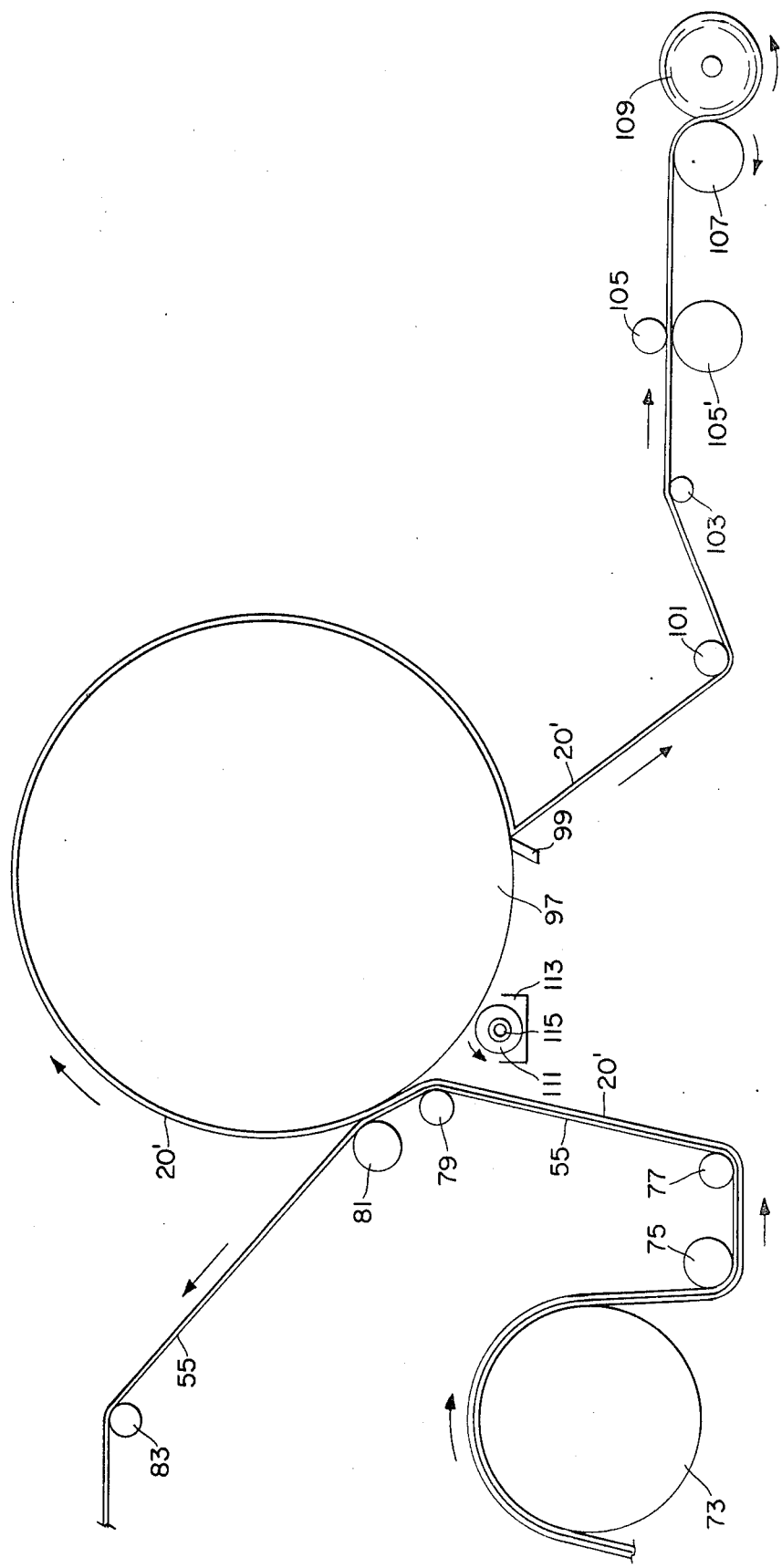

Another application of the Sanford and Sisson process which has been found to be particularly suitable for practice in conjunction with the instant invention is the twin-wire embodiment depicted in FIGS. 2A and 2B. The following description makes continuing reference to these two figures in which the thickness of some elements has been exaggerated for clarity. The precise details of the devices and apparatus used in the process will be readily apparent to those skilled in the art. It will also be apparent to those skilled in the art that numerous variations can be made in the described embodiment without departing from the spirit and scope of the Sanford and Sisson process.

Papermaking furnish comprising mixtures of fibers as hereinafter described is delivered from twin-wire headbox 11 to a forming zone adjacent forming roll 37 and contained between bottom forming wire 13 and top forming wire 53 and extending from twin-wire close point 117 to exit point 119 which is the point at which top forming wire 53 ceases to contact forming roll 37.

Bottom forming wire 13 moves in the direction indicated by the arrows and follows a travel path established by preforming roll 15, breaker roll 17, couch roll 19, return roll 21, bottom wire stretch roll 23, support roll 25, guide roll 27, and support roll 29. It passes over and around preforming roll 15, generally downward under forming roll 37 so as to define the lower portion of the forming zone hereinbefore described, moves generally upward toward breaker roll 17, passes over the top of breaker roll 17 and moves generally downward and in a direction away from preforming roll 15 toward couch roll 19. Bottom forming wire 13 then passes over and around couch roll 19, moves generally downward toward return roll 21, passes around and under return roll 21, moves toward bottom wire stretch roll 23, passes under and around bottom wire stretch roll 23, moves generally upward toward support roll 25, and passes over the top of support roll 25. It then moves generally horizontally toward guide roll 27, passes under and around guide roll 27, moves in an upward direction toward support roll 29, passes around and over support roll 29 and moves then toward preforming roll 15 where it begins to retrace the hereinbefore defined path.

Top forming wire 53 moves in the direction indicated by the arrows around the path defined by forming roll 37, top wire stretch roll 39, guide roll 41, guide roll 43, guide roll 45, and guide roll 47. After leaving exit point 119, top forming wire 53 moves in a generally upward direction past breaker roll 17 and toward top wire stretch roll 39, and then passes under, around, and over top wire stretch roll 39. After leaving top wire stretch roll 39, top forming wire 53 moves generally horizontally toward guide roll 41, passes under, around, and over guide roll 41, moves generally upward toward guide roll 43, passes under and around guide roll 43 and moves generally upward toward guide roll 45. Top forming wire 53 then passes around and over guide roll 45, moves generally downward toward guide roll 47, passes over and around guide roll 47, and moves generally downward toward forming roll 37. It passes around and under forming roll 37 from a point adjacent twin-wire close point 117 to exit point 119 thereby defining the upper portion of the forming zone hereinbefore described. It then retraces the hereinbefore defined path.

Both bottom forming wire 13 and top forming wire 53 can be constructed from foraminous materials, such as woven wire cloth, well known to those skilled in the art.

Paper web 20' is formed between bottom forming wire 13 and top forming wire 53 when furnish flows from twin-wire headbox 11 into the forming zone as hereinbefore defined. The paper web formed has a dry basis weight ranging, for example, from about 5 to about 20 pounds per 3,000 square feet. The fiber consistency in the twin-wire headbox 11 ranges from about 0.05 to about 0.50 percent (by weight on a dry fiber basis). After formation, the web travels between the two forming wires through the forming zone adjacent the underside of forming roll 37 where a portion of its water is expelled by centrifugal force. It travels between the two wires and with the two wires from exit point 119 to that position adjacent breaker roll 17 at which upper forming wire 53 is separated from the combination of paper web 20' and bottom forming wire 13. Moist paper web 20' then travels with bottom forming wire 13 to and around couch roll 19 and continues with bottom forming wire 13 during a portion of the latter's path between couch roll 19 and return roll 21.

Bottom wire vacuum transfer box 33, here depicted as a two-stage device, is positioned under bottom forming wire 13 adjacent foming roll 37 and intermediate forming roll 37 and breaker roll 17. Bottom wire vacuum transfer box 33 functions to draw water from web 20' through bottom forming wire 13. As a result of the action of bottom wire vacuum transfer box 33, web 20' is dewatered to provide a fiber consistency ranging, for example, from about 5 to about 10 percent. Bottom wire vacuum transfer box 33 also serves to force web 20' into intimate contact with bottom forming wire 13 thereby facilitating the subsequent separation of top forming wire 53 from moist web 20'.

Moist web 20' is transferred from bottom forming wire 13 to conveying and imprinting fabric 55 at a point intermediate couch roll 19 and return roll 21. After paper web 20' has transferred from bottom forming wire 13, bottom forming wire 13 continues along the path hereinbefore defined under and around return roll 21 and along the path defined by bottom wire stretch roll 23, support roll 25, guide roll 27, and support roll 29. During this path, bottom forming wire 13 passes under water sprays 35 located intermediate return roll 21 and bottom wire stretch roll 23 where it is washed. Vacuum box 31 is located intermediate support roll 29 and preforming roll 15 and serves to remove water from bottom forming wire 13.

In following the path previously described, top forming wire 53 passes under water sprays 49 at a point intermediate guide roll 41 and guide roll 43 where it is washed. Top forming wire 53 also passes over and is dewatered by vacuum box 51 which is located intermediate guide roll 45 and guide roll 47.

Conveying and imprinting fabric 55 moves in the direction indicated by the arrows along the path defined by guide roll 63, guide roll 65, guide roll 67, first sieve drying roll 69, turning roll 71, second sieve drying roll 73, guide roll 75, guide roll 77, guide roll 79, pressure roll 81, guide roll 83, guide roll 85, conveying and imprinting fabric stretch roll 87, guide roll 89, guide roll 91, and guide roll 93. In following its travel path, conveying and imprinting fabric 55 passes under guide roll 63, moves diagonally downward away from bottom forming wire 13, passes under guide roll 65, moves substantially horizontally toward guide roll 67, passes under guide roll 67 and turns upwardly thereabout, moves diagonally upward and passes over and around first sieve drying roll 69, moves diagonally downward toward turning roll 71, passes under and around turning roll 71, and moves diagonally upward over and around second sieve drying roll 73. It then moves diagonally downward toward guide roll 75, passes around and under guide roll 75, and moves substantially horizontally toward guide roll 77. After passing under and around guide roll 77, conveying and imprinting fabric 55 moves diagonally upward toward guide roll 79, passes around guide roll 79, moves generally upward toward pressure roll 81, passes about pressure roll 81, and moves generally upward toward guide roll 83. It passes over guide roll 83, moves generally horizontally toward guide roll 85, passes over, around and under guide roll 85, moves diagonally downward toward conveying and imprinting fabric stretch roll 87, passes over, around, and under conveying and imprinting fabric stretch roll 87, moves substantially horizontally toward guide roll 89, passes under guide roll 89, and moves diagonally upward toward guide roll 91. It passes over and around guide roll 91, moves diagonally downward toward guide roll 93, passes around guide roll 93, and moves diagonally downward adjacent couch roll 19 so as to be aligned with and adjacent the initial portion of the travel path of bottom forming wire 13 between couch roll 19 and return roll 21. Conveying and imprinting fabric 55 bears on and is turned downwardly by the surface of imprinting fabric vacuum transfer box 57. Conveying and imprinting fabric 55 then passes under guide roll 63 and begins to retrace the hereinbefore defined path.

Conveying and imprinting fabric 55 is the same as conveying and imprinting fabric 30 hereinbefore described in conjunction with the first embodiment of the Sanford and Sisson process.

Moist web 20' is transferred from bottom forming wire 13 to conveying and imprinting fabric 55 by imprinting fabric vacuum transfer box 57 which is positioned on the side of fabric 55 opposite moist web 20' and which is intermediate guide rolls 93 and 63. During the transfer operation, partially dewatered web 20' is separated from bottom forming wire 13 and is attached to conveying and imprinting fabric 55 and thereafter travels with conveying and imprinting fabric 55 through a portion of its travel path as hereinafter described.

Air trimming nozzles 59 are located intermediate imprinting fabric vacuum transfer box 57 and multi-stage vacuum box 61 and are positioned on the side of conveying and imprinting fabric 55 opposite that contacting web 20'. Air trimming nozzles 59 serve to trim the edges of web 20'.

Multi-stage vacuum box 61, depicted here as a three-stage vacuum box containing compartments within which the vacuum is independently adjustable, is positioned on the side of fabric 55 opposite that in contact with web 20' and is located intermediate imprinting fabric vacuum transfer box 57 and guide roll 63. Multi-stage vacuum box 61 functions to partially dewater web 20'.

As web 20' travels with conveying and imprinting fabric 55 between guide rolls 63 and 75 it is thermally dried. This drying is accomplished without mechanically contacting the web 20' by the use of first and second sieve drying rolls 69 and 73. These sieve drying rolls, and the associated apparatus which is not depicted, are fully described in the aforementioned U.S. Pat. No. 3,303,576 which has been previously incorporated herein by reference. It suffices to state that heated air is forced from the inside of sieve drying rolls 69 and 73 through web 20' and fabric 55 thereby thermally drying web 20' without mechanically compressing it. It should be noted that web 20' is in direct contact with sieve drying rolls 69 and 73 and is intermediate the surface of the sieve drying rolls and conveying and imprinting fabric 55. Web 20' is thermally predried to from about 30 to about 98 percent consistency.

Web 20', after having been thermally predried, continues with fabric 55 as it travels along its path under and around guide roll 77 and around guide roll 79 and thence upward until both reach pressure roll 81 where thermally predried web 20' is imprinted with the knuckle pattern of conveying and imprinting fabric 55 by pressure roll 81 acting against Yankee dryer 97 with thermally dried web 20' and conveying and imprinting fabric 55 intermediate the pressure roll 81 and Yankee dryer 97 surfaces. Web 20' is transferred to the rotating cylindrical surface of Yankee dryer 97.

After conveying and imprinting fabric 55 has been freed of thermally predried web 20', it continues along its path over guide roll 83, over, around and under guide roll 85 until it is washed with water sprays 95 at a point intermediate guide roll 85 and conveying and imprinting fabric stretch roll 87. It then passes over, around, and under conveying and imprinting fabric 87 and continues along the path hereinbefore described until it again passes adjacent couch roll 19 and picks up uncompacted moist web 20' from bottom forming wire 13 in the manner previously described.

After web 20' has been transferred to the rotating cylindrical surface of Yankee dryer 97, it is dried to its final fiber consistency should it not already be at such consistency. Web 20', while on rotating cylindrical surface of Yankee dryer 97, is generally exposed to a temperature in excess of 100° C. and normally less than about 180° C. After being creped from the surface of Yankee dryer 97 by doctor blade 99, dried web 20' passes under guide roll 101, over Mount Hope roll 103, between calendar rolls 105 and 105' which together make up a calendar stack, and is wound on pick-up reel 109 which is driven by driving roll 107.

The transfer of thermally predried web 20' from conveying and imprinting fabric 55 to the rotating cylindrical surface of Yankee dryer 97 is facilitated with the aid of a solution of adhering agent such as that hereinbefore described. The adhering agent solution is applied to the rotating cylindrical surface of Yankee dryer 97 by means of an air nozzle, a rotating adhesive applicator coil, and an adhesive vat. Adhesive applicator coil 111 rotates within adhesive vat 113 which is partially filled with adhering agent solution. Rotating coil 111 is coated with adhering agent solution as it rotates within vat 113. Adhering agent solution is blown from the surface of rotating coil 111 and is deposited on the rotating cylindrical surface of Yankee dryer 97 by means of air nozzles 115 located within rotating coil 111.

Modifications and adjustments of the foregoing description of a twin-wire embodiment of the Sanford and Sisson processes will be apparent to those skilled in the art.

Prior to the instant invention, the raw material entering the papermaking process has comprised conventional, chemically pulped wood fibers when the resulting paper web was to be incorporated into tissues, towels, sanitary or like products. The practice of the instant invention, however, depends upon the use of thermomechanical pulp in conjunction with the Sanford and Sisson process to obtain highly desirable low density, relatively high tensile strength paper web.

Thermomechanical pulping, which is sometimes known as Asplund pulping and pressure refiner pulping, has been used for a number of years to make pulp used in the production of newsprint and fiberboard. While the basic thermomechanical pulping process well known in the art is used to make pulp for the practice of the instant invention, certain modifications in the basic process can be used to advantage.

In thermomechanical pulping, trees are reduced to chips and are washed by means well known in the art and are usually placed in a storage bin. From the storage bin the chips are conveyed, as by a screw conveyor, into a steam chamber or pre-heater. Steam is introduced into the steam chamber to raise the temperature of the chips and to properly condition (pretreat) them for subsequent refining operations. From the steam chamber the chips are conveyed, as by a screw conveyor, to a defibering unit which is commonly a pressurized single disc refiner or defibrator well known in the art. An example of a suitable pressurized single disc refiner is Model RLP 50/54S distributed by American Defibrator, Minneapolis, Minnesota. During treatment in the pressurized single disc refiner, in which the pulp consistency is typically 30 percent, the wood chips are reduced to pulp consisting primarily of single fibers and of small bundles of multiple fibers. Pressurized defiberazation is carried out under conditions such that the production of fiber fines and other debris is minimized. The object of this operation is to produce a pulp which consists primarily of single, undamaged, fibers. After leaving the pressurized single disc refiner, the pulp is discharged through a valve into a cyclone where the steam is withdrawn. In the normal thermomechanical pulping process, the pulp at this point normally is conveyed to a non-pressurized single disc refiner well known in the art. However, it has been found in the practice of the instant invention that second stage refining can be omitted and thus the pulp can be sent directly to the next stage of the manufacturing process.

Optionally, the chips can be soaked in a solution comprising sodium sulfite, sodium bisulfite, sulfur dioxide, sodium hydroxide, sodium peroxide or mixtures thereof, before or during pretreating, to enhance pulp color or susceptability to bleaching. For convenience of reference, pulp made from chips so soaked will be called chemithermomechanical pulp in this specification.

When the single disc pressurized defibrator operates at a temperature in excess of approximately 140° C., the lignin is softened so that the wood structure is broken in the lignin-rich middle lamella section and the fibers are almost completely separated in an undamaged condition. This phenomenon possibly results because at temperatures in excess of about 140° C., the lignin undergoes what is termed either a glass transition or thermal softening. The fibers, which are released intact, are coated with the softened lignin. On cooling, the lignin reverts to the glassy state and tends to encase the individual fibers and solidified lignin coating.

If the pressurized refiner is operated at a temperature in the range of from about 120° to about 130° C., most of the lignin, although it is softened, remains in the glassy state. At these lower temperatures, fractures occur in significant part during defiberizing in the outer layers of the secondary fiber wall. The net result is that the released individual fibers are coated with lignin in the glassy state, as in higher temperature pressure refining, but this glassy coating is characterized by gaps and fractures.

For the practice of the instant invention, it is preferred that the thermomechanical pulping or pressurized refining take place at a temperature of from about 120° to about 140° C., and most preferably at from about 120° to about 130° C. The preferred range of concentrations of wood fibers during pressurized refining is from about 20 to about 50 percent. The fibers issuing from the thermomechanical pulping process, in contrast to those fibers produced by conventional chemical pulping processes, contain most of the lignin of the native wood. Because of this they do not become as limp and as soft when they are wetted as do chemically pulped fibers.

Chemically pulped fibers are plasticized somewhat by water and, when subjected to the forces of papermaking, tend to collapse from their natural tubular structure into flat, ribbon-like elements. Thermomechanically pulped fibers, which because of their lignin content are not plasticized by water, retain in large measure their natural tubular, semi-rigid structure.

In the thermomechanical pulping process, and especially in the herein preferred version of that process which omits second stage refining, the fracture and fibrulation of lignin-containing fibers is held to a minimum thereby resulting in a pulp with a modified Canadian standard freeness (CSF) of from about 500 to about 750. (CSF is measured by the procedure of Standard T227m-58 of the Technical Association of the Pulp and Paper Industry, incorporated herein by reference, modified to include dispersion of the pulp from 10 to 15 minutes at from about 70° to about 90° C.) Significantly, most of the fibers issuing from the thermomechanical pulping process remain essentially intact and are coated to a greater or lesser degree, depending upon the temperature of the initial pulping operation, with lignin. It is, of course, inevitable in any mechanical pulping operation that some fibers will be broken or split and that some finite quantity of fines will be generated. In the preferred thermomechanical pulping process, the generation of fines is kept to a minimum consistent with economical operation of the process.

The bleaching stage is the next step in the process. Here, the pulp is chemically treated, as described hereinafter, in order to improve the color of the pulp and to improve its hydrophilicity.

A convenient way to quantitatively express fiber surface hydrophilicity is by the contact angle between a fiber and a droplet of water on the fiber. Contact angle is defined, at an equilibrated water-air-fiber interface, as the angle, measured in the liquid, of contact between the water and the fiber. A perfectly wetted fiber will have a contact angle of zero °. In general, if the contact angle is greater than 90°, the fiber is said to be hydrophobic and water will not wet the fiber; in this case droplets of water tend to move about easily on the surface of the fiber and will not enter capillary pores. The term "hydrophilic" generally refers to the surfaces wherein the contact angle is less than 90°. Preferably, and as used herein, "hydrophilic" is used to describe fibers which are characterized by a contact angle of less than about 75°. It should be noted that a variety of laboratory techniques for measuring contact angles have been developed. Since the specific analytical procedure used determines the value of the contact angle, there is a great deal of variability in reported contact angle values. Thus, the designation of 75° as a limitation on the definition of "hydrophilic" is intended solely as a guide to the type of behavior to be expected relative to conventional chemically pulped, delignified fibers.

The bleaching of thermomechanically processed pulp to improve its color and hydrophilicity can be accomplished by a number of procedures well known in the art. A preferred procedure is that generally described as peroxide bleaching.

A typical peroxide bleaching scheme employs the steps of pretreating, bleaching, washing and neutralizing. The pretreating step is desirable because of the susceptability of peroxide to catalytic decomposition by metallic ions. Thermomechanical pulps which contain large amounts of metallic ions or which are contaminated by free metallic ions will especially benefit from the pretreatment. Dilute solutions of either acid or chelating agents are typically used to complex or chelate free metallic ions. Dilute solutions of sulfuric acid or ethylenediaminetetraacetic acid are useful pretreating agents. The thermomechanical pulp is merely contacted with the pretreating agents at any convenient fiber consistency.

Following the pretreatment step, the thermomechanical pulp can be prepared for the actual bleaching operation by washing with a neutralizing solution of deionized water.

The bleaching step itself involves contacting the wood pulp with a peroxide solution. A suitable peroxide solution comprises about 5 percent (by weight of dry fiber) sodium silicate, about 0.05 percent epson salts (magnesium sulfate) and from about 2 to about 4 percent hydrogen peroxide. In the bleaching solution, which is prepared by codissolving the components, the epson salts and the sodium silicate function as stabilizers and pH buffers. The thermomechanical pulp is treated at from about 3 to about 20 percent fiber consistency at about 140° F. (60° C.) for from about 1 to about 3 hours. Sodium hydroxide is added during the bleaching step to maintain pH in the range of about 10.0 ±0.5. Rapid and thorough mixing of the bleach solution and thermomechanical pulp is essential as is the careful control of temperature and pH.

The complex chemical reactions which take place during the bleaching operation are not completely understood. It is, however, believed that the primary reaction is a selected oxidation (with its accompanying decolorization) of the naturally occuring organic coloring agents associated with the lignin surrounding the fibers.

After the bleaching operation is completed, the bleached thermomechanical pulp is washed as with deionized water and is neutralized to a pH of from about 4 to about 7, preferably with sulfurous acid.

Variations in the above described bleaching operation, as well as the selection of the particular equipment in which to accomplish the operation, will be readily apparent to those skilled in the art. A more detailed discussion of the parameters of peroxide bleaching is contained in *The Pulping of Wood, Volume* 1, 2nd Edition, R. G. McDonald, Editor, McGraw-Hill Book Company (New York, 1969), incorporated herein by reference.

In addition to increasing the hydrophilicity in the thermomechanical pulp, peroxide bleaching also serves to significantly lighten the color of the pulp fibers thereby making products made from the thermomechanical pulp more aesthetically pleasing. Additional bleaching stages, including the well known hydrosulfite, ozone, or peracetic acid bleaching processes, can be employed as necessary to meet special requirements of the products for which the thermomechanical pulp is intended.

The furnish used in forming the web of this invention comprises from about 5 to about 70 percent (by weight of total dry fiber) thermomechanically pulped fibers which have preferably been bleached. There can be present substantial quantities of conventional chemically pulped fibers. The preferred range of thermomechanically pulped fibers is from 20 to 50 percent by weight of the total fiber content. Both the thermomechanical pulp and the conventional chemical pulp can be obtained from any wood source, either softwood (gymnosperm) or hardwood (angiosperm). Preferably, the conventional chemical pulp is obtained primarily from softwood by means of the kraft process well known to those skilled in the art.

In addition to the aforementioned fibers, the furnish can contain the usual papermaking additive chemicals such as dyes, pigments, wet-strength resins, dry-strength resins, and surface active agents. The nature of the final product made from the web controls the selection of the specific additive papermaking chemicals used. By way of example, and not of limitation, additive papermaking chemicals which can be used in this process include Parez 631NC, a polyacrylamide made by American Cyanamid Company, Wayne, New Jersey; Kymene 557, a polyamideepichlorohydrin complex made by Hercules, Inc., Wilmington, Delaware; Pegosperse 200 ML, a polyethyleneglycol monolaurate made by Glyco Chemicals, Inc., Greenwich, Connecticut; and Tydex 12, a polyethylenimine made by the Dow Chemical Company, Midland, Michigan.

In order to more completely describe the instant invention, and not by way of limitation, the following examples are presented.

EXAMPLE I

To demonstrate the unexpected tensile-density response obtained by the use of this invention, handsheets comprising thermomechanically pulped and chemically pulped fibers were prepared.

Handsheets are handmade test specimens of paper made using laboratory scale equipment which simulates papermaking machinery. Two different procedures are used: one simulates the so-called conventional papermaking process while the other simulates the Sanford and Sisson process. The procedures used in this example are freely adapted from Standard T 205 os-71 of the Technical Association of the Pulp and Paper Industry and from Standard C.4 of Technical Section of the Canadian Pulp and Paper Association, both of which Standards are incorporated herein by reference.

In the handsheet method which simulates the Sanford and Sisson process, 2.5 grams (dry basis) of pulp are mixed with 1500 ml tap water at from about 73° to about 78° F (22.8°–25.6° C.) and are dispersed for about 5 to about 10 minutes in any convenient dispersing device such as the revolving blade disintegrator described in the hereinbefore incorporated Standards. The dispersed pulp is then added to the hereinafter described deckle box.

The actual handsheet is formed in a deckle box which is similar to the sheet machine of the hereinbefore incorporated Standards. The deckle box used is a 12 inch (30.5 cm) square container with a valved drain beneath a securing means which holds a paper forming wire in place. Pulp slurry and water are added to the deckle box, the slurry is agitated, the valve in the drain is opened and the fluid is allowed to drain through the secured papermaking wire which retains the fibers thereby forming a wet paper web. In operation, the papermaking wire hereinafter described, is secured in the bottom of the deckle box above the drain and water is added to the box to a height of about 8.5 inches (21.6 cc) above the wire. The slurry of pulp is added to the deckle box and thoroughly mixed using a perforated metal plunger. The valve is then opened thereby allowing water to run from the deckle box forming a fiber mat on the papermaking wire.

The papermaking wire is a woven monel wire cloth of 100 mesh made from 0.0045 inch (0.11 mm) diameter wire.

Immediately after the web is formed, it is removed from the deckle box with its supporting papermaking wire and is drawn across a 13 inch by 1/16 inch (33.0 by 0.16 cm) slot in a vacuum box in which the vacuum is maintained at 4 ±0.5 inches Hg (10.2 ±1.3 cm Hg) below atmospheric pressure with the moist web uppermost so as to dewater the web without mechanically compressing it. The vacuum in the vacuum box is then adjusted to 10 ±0.5 inches Hg (25.4 ±1.3) cm Hg). An imprinting fabric, as hereinafter described, is placed near the opening in the vacuum box and the papermaking wire with the partially dewatered web on its upper surface is inverted and placed on the imprinting fabric so as to form a combination, from bottom to top, of imprinting fabric, partially dewatered web, and papermaking wire. This combination is drawn across the slot in the vacuum box so as to transfer the partially dewatered web to the imprinting fabric and to further dewater the web.

The imprinting fabric is woven from polyester filaments 0.016 inches (0.4 mm) in diameter in a 36 × 30 filament per inch mesh.

The web on the imprinting fabric is now dried without mechanical compression by means of a cylindrical drum dryer, which is 13 inches (33.0 cm) in diameter, is steam heated to a surface temperature of 235° C., and which revolves at 0.9 rpm. The portion of the surface of the drum available for drying is that portion defined by a central angle of 263°.

The method of making handsheets which simulates the conventional papermaking process is identical to that which simulates the Sanford and Sisson process down to the point at which the papermaking wire and its associated fiber web is removed from the deckle box. After being removed from the deckle box, the wire with its associated fiber web is inverted and placed, web side down, on a damp papermaking felt. Papermaking felt is placed over the papermaking wire thereby forming a combination comprising, from bottom to top, damp papermaking felt, wet fibrous web, papermaking wire, and damp papermaking felt. This combination is passed between the rolls of a two-roll press wherein the pressure is maintained is about 91 pounds per linear inch (16.3 Kg per linear cm). The combination is removed from the press and the top papermaking felt is removed. The papermaking wire with the adhering mechanically compressed fibrous web, is removed from the bottom papermaking felt, inverted so that the fibrous web is on the uppermost surface, and is dried by the hereinbefore described drum dryer with papermaking wire adjacent the rotating cylindrical surface of the drum dryer.

The pulps used in the hereinafter described Furnish A and Furnish B are northern softwood kraft, hardwood sulfite, hemlock sulfite, and red alder thermomechanical pulps. Northern softwood kraft pulp is prepared by the well known kraft process from, as its name implies, northern softwoods. The hardwood sulfite pulp is produced by the well known sulfite process and is a mixture of hardwoods typically comprising oak, maple, and beech in essentially equal amounts along with lesser amounts of birch, ash, and poplar. The hemlock sulfite pulp is also prepared by the well known sulfite process but comprises essentially 100 percent hemlock fibers. The thermomechanical pulp used in this example was supplied by the Weyerhaeuser Company, Everett, Washington. It was prepared by the hereinbefore described thermomechanical pulping process with the initial defibration occuring at from about 130° to about 140° C. The thermomechanical pulp was lightly refined in a second stage refiner to a modified Canadian standard freeness of approximately 575 cc and was bleached by the hereinbefore described peroxide method. As supplied by the Weyerhaeuser Company, thermomechanical and the hemlock sulfite pulps were mixed in the weight ratio of 8:2.

Furnish A comprised 60 percent (by weight dry fiber basis) northern softwood kraft, 8 percent hemlock sulfite, and 32 percent thermomechanical pulps. The northern softwood kraft pulp was refined for 10 minutes at 2.0 percent consistency in a Valley Beater Model No. SO1125, a pulp refiner well known in the art made by Allis Chalmers Co., Paper Machinery Division, Appleton, Wisconsin.

Furnish B comprised 60 percent northern softwood kraft and 40 percent hardwood sulfite pulps.

Both Furnish A and Furnish B were used in handsheets made by each of the hereinbefore described methods simulating conventional papermaking processes and the Sanford and Sisson papermaking process. The basis weight, bulk density, and dry tensile strength (one direction) values reported in Table 1 are the averages of four individual handsheets.

TABLE 1

| Method | Conventional | | Sanford & Sisson | |
|---|---|---|---|---|
| Furnish | A | B | A | B |
| Bulk Density, g/cc | 0.156 | 0.235 | 0.103 | 0.131 |
| Tensile, g/in | 870 | 1195 | 1265 | 770 |
| Basis Wt., lb/3000 ft² | 17.1 | 17.2 | 16.5 | 16.5 |

FIG. 3 is a graphical representation of the relationship between bulk density as the independent variable and dry tensile strength as the dependent variable for the handsheets of Example I. It is apparent from FIG. 3 that the 3 data points representing handsheets made by the method representing conventional papermaking processes from both Furnish A and Furnish B and the handsheet made by the method simulating the Sanford and Sisson process from Furnish B can be fairly represented by the single straight line indicated. The handsheet made by the method simulating the Sanford and Sisson process and using Furnish A, which contained 32% thermomechanical pulp, is significantly different from this line. This significant difference exemplifies a relationship between the Sanford and Sisson process and thermomechanical pulp which can be described as synergistic rather than additive.

EXAMPLE II

A web comprising thermomechanical pulp was formed using the hereinbefore described twin-wire embodiment of the Sanford and Sisson process illustrated in FIGS. 2A and 2B.

Furnish A of Example I was used as the starting point for the papermaking furnish of this Example II. To the combination of 60 percent (by weight, dry fiber basis) northern softwood kraft, 8 percent hemlock sulfite, and 32 percent red alder thermomechanical pulps, was added 20 pounds (9.08 kg) Parez 631 NC resin per ton (908 kg) of fiber and 1 pound (0.4 kg) Pegosperse 200-ML per ton (908 kg) of fiber. The papermaking furnish was maintained at 0.25 percent fiber consistency and the pH was maintained at 6.5.

Flow from the headbox into the forming zone between the top and bottom forming wires, each traveling at 800 feet per minute (243.8 meters per minute), was adjusted so as to form a uniform, moist paper web having a dry basis weight of 13.3 pounds per 3,000 square feet (21.7 grams per square meter).

The web formed between the two forming wires was dewatered in the forming zone to approximately 8 percent fiber consistency. The vacuum in the two stages of the bottom wire vacuum transfer box was maintained at 0.75 and 2.0 inches Hg (1.90 and 5.08 cm Hg) respectively.

The top and bottom forming wires were made of polyester strands, 0.2 mm in diameter. Each wire was woven four shed with 78 warp and 62 shute strands per inch.

The partially dewatered moist web was transferred to the conveying and imprinting fabric with the aid of the imprinting fabric vacuum transfer box which was maintained at a vacuum of 6 inches Hg (15.2 cm Hg). The conveying and imprinting fabric was a semi-twill material having a free span of 19.4 mils (0.5 mm) with 31 warp strands and 25 shute strands per inch. The warp strands were 0.45 mm in diameter and the shute strands were 0.50 mm in diameter and were made from polyester. Further dewatering of the web was accomplished by the multi-stage vacuum box wherein the three stages were maintained at vacuums of 9 inches, 10 inches, and 11.5 inches Hg (22.9, 25.4, and 29.2 cm Hg) respectively.

The moist web on the conveying and imprinting fabric was predried to 57.7 percent fiber consistency in the hot air drying section (i.e., the portion of the process comprising the two sieve drying rolls) by passing hot air through the moist web and the conveying and imprinting fabric. Air at a temperature of about 275° F. to about 375° F. (135°–191° C.) was used. The thermal predrying was accomplished without mechanically compressing the moist web.

The thermally predried web was imprinted with the fabric knuckle pattern and was transferred to the rotating cylindrical surface of the Yankee dryer with the air of the pressure roll. The adhesion of the web to the rotating cylindrical surface of the Yankee dryer was aided by an animal glue adhesive applied to the surface of the Yankee dryer at the rate of 100 grams of 0.5 percent solution per minute to the 20 inch (50.8 cm) width of the Yankee which rotated with a surface speed of 800 feet per minute (243.8 meters per minute).

The imprinted paper web adhered to the rotating cylindrical surface of the Yankee dryer was dried to a fiber consistency of about 97 percent and was removed from the Yankee by means of a conventional doctor blade having a 30° bevel and aligned at 37° from the tangent to the Yankee. The Yankee dryer was heated with saturated steam at 100 psig (7.8 atm). The dried, creped sheet was removed from the doctor blade at 632 feet per minute (192.6 meters per minute) by a pick-up reel revolving at such a rate that the product retained 21 percent crepe.

The final product had a basis weight of 16.8 pounds per 3,000 square feet (27.4 grams per square meter). The dried, creped web had a caliper of 16.9 mil (0.04 mm), dry tensile strength in the machine direction of 543 grams per inch, dry tensile strength in the cross-machine direction of 449 grams per inch, and a bulk density of 0.063 g/cc.

When the web was made into a two-ply paper towel following the teachings of Wells in U.S. Pat. No. 3,414,459 issued Dec. 3, 1968, incorporated herein by reference, a 13.8 percent increase in absorbency, relative to a two-ply towel composed of webs made in a manner similar to the Example but using Furnish B of Example I, was observed.

Another aspect of this invention has been briefly alluded to supra. Thermomechanical pulp can be made from chips which have been pretreated (soaked) in mild chemical solutions; this pulp will be referred to for convenience in this specification as "chemi-thermomechanical pulp". Chemi-thermomechanical pulp is then bleached (treated) with ozone to imrpove its surface hydrophilicity, color, and to impart special characteristics to the surface of the pulp. A second bleaching operation may optionally be used to further improve the color of the pulp. Blending this ozone-treated chemi-thermomechanical pulp with conventional softwood chemical pulp and using the furnish so formed in the Sanford and Sisson process results in low density paper webs with significantly improved burst and tear properties.

Burst strength is a measure of the ability of a paper web to resist rupture when an element is forced against the plane surface of the web. In measuring burst strength, the sample is moved downwardly onto the uppermost portion of an upwardly extending plunger. The force required to cause the plunger to rupture the web, measured in grams, is the burst strength of the web. The plunger which is used to rupture the paper web is approximately 10.8 centimeters long, is constructed of any convenient rigid metal such as stainless steel, and is terminated with a spherical end piece 1.588 centimeters in diameter. It is the spherical end piece which contacts the paper web being tested. The plunger is connected by the end opposite the spherical end piece to a means for measuring and/or recording force. A particularly suitable means is one of the various compression load cells well known to those skilled in the art and manufactured by the Instron Corporation of Canton, Massachusetts.

The sample of paper web to be tested for burst strength is secured in a sample holder. This sample holder comprises two rigid planar elements, each of which is provided with a circular opening 8.89 centimeters in diameter. Means are provided to securely fasten the two planar elements together so that the circular openings are superposed with the paper web to be tested interposed between them. The web must, of course, be exposed over the whole of the area defined by the circular openings in the two planar elements.

Means are provided to securely mount the compression load cell with the plunger attached so that the spherical end piece extends vertically upward. Means are also provided to cause the exposed web in the sample holder to be moved downward over the spherical end piece at a constant rate of 12.7 centimeters per minute. The paper web and the plunger must be so arranged that the spherical end piece of the plunger engages the paper web in the center of the area defined by the circular openings in the two planar elements of the sample holder. The Universal Testing Machine well known to those skilled in the art and manufactured by the Instron Corporation is admirably suited to serve these purposes.

Any suitable means well known to those skilled in the art can be provided to measure and/or record the force required to cause the paper web to be ruptured by the plunger's spherical end piece.

Tear strength is the measure of the ability of the paper web to resist tearing. Tear testing is conducted in accordance with ASTM Standard Method D689-62, which is equivalent to TAPPI Method T414, both of which methods are incorporated herein by reference.

Chemi-thermomechanical pulp is made from wood chips which have been washed. The washed chips are removed from the conventional chip storage bin and are conveyed by any suitable means to either an optional preheater or directly to a treatment unit. If the optional preheater, which can be any suitable vessel, is used, wood chips and steam are introduced; the preheater is maintained at atmospheric pressure. In the preheater, the temperature of the chips is raised from ambient up to any desired level below about 99° C. The purpose of the preheater is to raise the temperature of the chips thereby reducing the energy load on the treatment unit and to expel air from the chips.

From the optional preheater (or from the chip storage bin if the optional preheater is not used) chips are conveyed by any suitable means to a treatment unit. Such a suitable means is a screw conveyor which tends to compress the chips. Not only does such a device move the chips and seal the treatment unit against pressure loss, but the device also materially aids in the impregnation of the chips during the treating step. The chips are compressed in the screw conveyor and are discharged in that condition into the treatment unit below the surface of the treatment liquor therein. When the pressure on the chips is reduced as the chips are introduced into the treatment unit, the chips expand and absorb treatment liquor.

During the treating step conducted in the treatment unit, the chips are both impregnated with treatment liquor and maintained at elevated temperature and pressure for a prescribed period of time.

One suitable treatment unit is a pressure vessel provided with an upper pool of treatment liquor, a lower holding chamber, and a means for conveying chips from the upper pool to the lower chamber. This means can be, for example, a screw conveyor which removes chips from the upper pool and carries them to a point where they will fall by gravity through the atmosphere within the treatment unit into the lower chamber.

An alternate arrangement of the treatment unit can comprise two vessels in series. In the first, the chips are impregnated with treatment liquor at any convenient temperature by steeping therein for from about 5 to about 25 minutes. The impregnated chips are then conveyed to the second vessel wherein they are subjected to an elevated temperature.

While such arrangements as just described are suitable for use in making the chemi-thermomechanical pulp useful in the instant invention, they are not the only designs that may be so used. Design and construction of suitable processes are well within the ability of a skilled artisan having before him the teachings of the instant specification.

The temperature within at least a portion of the treatment unit is maintained at from about 124° C. to about 185° C. The pressure within the treatment unit is that steam pressure which corresponds to that temperature. The average residence time of a chip at the elevated temperature is from about 5 to about 120 minutes.

During their residence within the treatment unit, the wood chips are impregnated with a quantity of treatment liquor. The quantity of treatment liquor absorbed by the chips is dependent upon the species of wood, the previous history of the chips, and upon the exact equipment used. Typically, for the equipment described above, the wood chips are impregnated with from about 0.5 kg. of liquor to about 2 kg. of liquor per kg. of bone dry chips.

The treatment liquor used during the treating step is an aqueous chemical solution which facilitates the defibration of the wood chips in the subsequent defibrating step. In the first arrangement described above, chemicals, heated water under pressure, and steam are introduced directly to the upper pool of the treatment unit. In the alternate arrangement, chemicals and water are introduced into the first vessel and steam into the second vessel.

The treatment liquor contains from about 5 to about 30% by weight of sodium sulfite, sodium bisulfite, and/or sodium carbonate in varying proportions. The exact composition of the treatment liquor will depend upon the species of wood used. The selection of an appropriate composition is well within the ability of one skilled in the pulping art.

From the treatment unit, the pulp passes to the defibrator. Defibration is usually accomplished at from about 124° C. to about 160° C. at a consistency of about 25 ± 5% by weight. Water can be added to the treated chips just prior to their entry into the defibrator to adjust the consistency. Conveniently, the transfer of the treated chips from the treatment unit to the defibrator is accomplished with a screw conveyor. The pressure within the defibrator is commonly only slightly less than the pressure within the treatment unit.

The defibrator can be any of the well known units used in the manufacture of thermomechanical or Asplund pulp such as the one described supra. Defibrators are normally operated in such a manner that damage to the fibers is minimal. Power input to the defibrator is controlled so as to achieve essentially complete defibration with minimal damage to the fibers.

From the defibration unit, the pulp passes to the ozone treatment unit where it is treated with ozone.

The ozone treatment of the chemi-thermomechanical pulp can be accomplished in any suitable equipment the design of which will be readily apparent to those skilled in the art.

The pulp issuing from the defibrator is formed into sheets having a consistency of from about 40% to about 50% by weight based on bone dry pulp. The pulp sheets are fed to a continuous mechanical fluffer and then into the ozone reactor. Ozone at from about 1 to about 6% by weight based on bone dry pulp is introduced into the ozone reactor. Ozone and fluffed pulp are contacted at a temperature of from about 40° to about 55° C. until essentially all the ozone is reacted.

Following ozone treatment, the pulp is reslurried in water at a consistency of about 3%. From about 1% to about 4% by weight of bone dry pulp sodium hydroxide and from about 0.1% to about 0.5% DTPA (diethylenetriamine pentaacetic acid) can optionally be added to the reslurried pulp.

Following ozone treatment, the pulp is bleached in a single stage with peroxide as hereinbefore described.

After the bleaching operation is completed, the ozone-treated chemi-thermomechanical pulp is washed with deionized water and is neutralized to a pH of from about 2 to about 7, preferably with sulfurous acid.

In the practice of this aspect of the present invention, the ozone-treated chemi-thermomechanical pulp is blended with conventional softwood chemical pulp. Preferably, the softwood chemical pulp is made by the kraft process from a mixture of northern softwoods. This preferred pulp is commonly referred to in the art as Northern Softwood Kraft Pulp. From about 5% to about 70% ozone-treated chemi-thermomechanical pulp, by weight on a bone dry fiber basis, is present in the furnish.

In the following example, the ozone-treated chemi-thermomechanical pulp was made from a mixture of maple and oak wood chips (nominally 1.6 cm chips) which had been steamed in a pretreatment unit at atmospheric pressure for 10 minutes prior to further treatment. The steamed chips were impregnated with about 0.8 kg of treatment liquor per kg of chips. The treatment liquor comprised 18.6% by weight sodium sulfite. The impregnated chips were maintained at 150° C. for 30 minutes prior to defibrating with a power input of about 8 horse power days per ton of bone dry pulp. The ozone treated pulp was bleached in a single stage with peroxide at a consistency of 15% by weight. The bleaching solution comprised 0.05% by weight magnesium sulfate and sodium sulfite with a total alkalinity expressed as $Na_2O$ of 5%. The peroxide concentration was 4%. The bleaching was continued for two hours at 93° C. Following the bleaching, the pulp was washed and neutralized with sulfurous acid to a pH of 2.5.

EXAMPLE III

Handsheets were made by the method which simulates the Sanford and Sisson process as described in Example I. The pulp furnish comprised the ozone treated chemi-mechanical pulp ($O_3$-CTMP) immediately hereinbefore described and Northern Softwood Kraft (NSK) pulp. The relative amounts of the two pulps were as shown in Table 2. The burst and tear strengths of the handsheets were measured and the results, corrected for any difference in basis weight, shown in Table 2 were obtained.

TABLE 2

| NSK | $O_3$-CTMP | Burst | Tear |
| % by weight | | g | g |
| --- | --- | --- | --- |
| 100 | 0 | 255 | 28 |
| 75 | 25 | 300 | 30 |
| 60 | 40 | 317 | 35 |
| 50 | 50 | 312 | 38 |
| 40 | 60 | 273 | 33 |
| 25 | 75 | 265 | 18 |
| 15 | 85 | 220 | 20 |
| 0 | 100 | 218 | 10 |

It can be readily seen from Table 2 that the effects of blending ozone-treated chemi-thermomechanical pulp with conventional chemical pulp in the Sanford and Sisson papermaking process is synergistic. That is to say, the effects are more than additive. The burst strength of paper made with 100% conventional chemical pulp is, in this example, 255 grams, while the burst strength of paper made with 100% ozone treated chemimechanical pulp is 218 grams, a substantially lower value than obtained with 100% conventional chemical pulp. Adding as little as 25% ozone treated chemi-thermomechanical pulp to the conventional chemical pulp increases the burst strength of the paper to 300 grams, rather than decreasing it as would be expected if the results were additive rather than synergistic. The synergistic effect obtains until the ozone treated chemi-thermomechanical pulp comprises about 70% of the total fiber furnish. At that point, the burst strength of the paper web formed from the furnish becomes less than that of a web formed from 100% conventional chemical pulp. Similar results and conclusions can be obtained from an examination of the tear values shown in Table 2.

What is claimed is:

1. A process for making soft, bulky, absorbent paper webs which comprises the steps of:
   a. supplying an aqueous papermaking furnish comprising from about 5% to about 70% by weight of total fiber chemi-thermomechanical pulp having a modified Canadian standard freeness from about 500 to about 750 cc and consisting essentially of intact and lignin coated fibers, wherein said chemi-thermomechanical pulp has been prepared by treating wood chips with a liquor containing chemicals selected from the group consisting of sodium sulfite, sodium bisulfite, sodium carbonate, and mixtures thereof prior to defibration, and wherein said chemi-thermomechanical pulp has been treated with ozone subsequent to defibration;
   b. forming an uncompacted paper web from said papermaking furnish;
   c. supporting said uncompacted paper web on a conveying and imprinting fabric;
   d. thermally predrying said uncompacted paper web to a fiber consistency of from about 30% to about 98%;
   e. imprinting the knuckle pattern of said conveying and imprinting fabric into the thermally predried uncompacted paper web; and
   f. finally drying the web so formed.

2. The process of claim 1 wherein said chemi-thermomechanical pulp which has been ozone treated has been subsequently bleached.

3. The process of claim 1 wherein said furnish comprises from about 25% to about 50% by weight of total fiber chemi-thermomechanical pulp which has been ozone treated.

4. The process of claim 3 wherein said chemi-thermomechanical pulp which has been ozone treated has been subsequently bleached.

5. The soft, bulky, absorbent paper web was made by the process of claim 1.

6. The soft, bulky, absorbent paper web made by the process of claim 2.

7. The soft, bulky, absorbent paper web made by the process of claim 3.

8. The soft, bulky, absorbent paper web made by the process of claim 4.

* * * * *

UNITED STATES PATENT OFFICE
CERTIFICATE OF CORRECTION

PATENT NO. : 4,120,747
DATED : October 17, 1978
INVENTOR(S) : Henry David Sarge, III
David Charles Kleinschmidt It is certified that error appears in the above-identified patent and that said Letters Patent are hereby corrected as shown below:

Claim 5, line 1, "was" should be deleted.

Signed and Sealed this

Sixth Day of March 1979

[SEAL]

Attest:

RUTH C. MASON
*Attesting Officer*

DONALD W. BANNER
*Commissioner of Patents and Trademarks*